United States Patent [19]

Stefanska et al.

[11] Patent Number: 4,824,944

[45] Date of Patent: Apr. 25, 1989

[54] ANTINEOPLASTIC ENAMINE DERIVATIVES OF DAUNORUBICIN AND ADRIAMYCIN

[75] Inventors: Barbara J. Stefanska; Leonard S. Falkowski; Edward Borowski, all of Gdansk, Poland

[73] Assignee: Politechnika Gdanska, Gdansk, Poland

[21] Appl. No.: 2,050

[22] Filed: Jan. 12, 1987

Related U.S. Application Data

[63] Continuation-in-part of Ser. No. 627,443, Jul. 3, 1984, abandoned.

[51] Int. Cl.[4] .......................................... C07H 15/24
[52] U.S. Cl. ........................................................ 536/6.4
[58] Field of Search ........................................... 536/6.4

[56] References Cited

U.S. PATENT DOCUMENTS 4,591,637  5/1986  Acton et al. ......................... 536/6.4

Primary Examiner—Johnnie R. Brown
Assistant Examiner—Elli Peselev
Attorney, Agent, or Firm—Ladas & Parry

[57] ABSTRACT

The present invention relates to new enamine derivatives of daunorubicin and adriamycin of the formula 1:

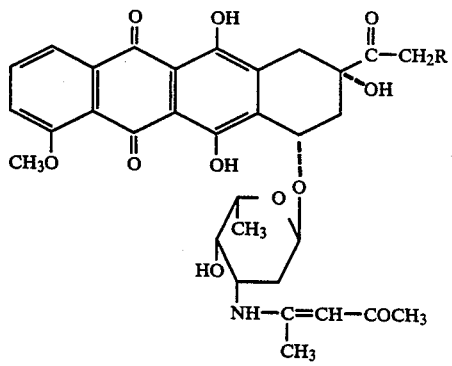

and formula 2:

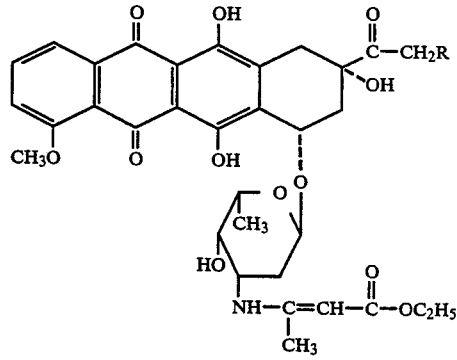

wherein R denotes a hydrogen atom or hydroxyl group. The inventive compounds are useful antineoplastic antibiotics utilized in the treatment of cancer, primarily leukemia. The present derivatives demonstrate a reduction in toxicity, in particular cardiotoxicity, over their parent compounds, while retaining chemotherapeutic properties.

1 Claim, No Drawings

ANTINEOPLASTIC ENAMINE DERIVATIVES OF DAUNORUBICIN AND ADRIAMYCIN

This application is a continuation-in-part of applicant's copending U.S. Ser. No. 627,443 filed July 3, 1984, now abandoned.

BACKGROUND OF THE INVENTION

This invention concerns new enamine derivatives of daunorubicin and adriamycin having the general formula 1 and 2, wherein R denotes a hydrogen atom or a hydroxyl group. The inventive derivatives are usefyl antineoplastic antibiotics utilized in the treatment of cancer, primarily leukemia. The present compounds demonstrate a reduction in toxicity, in particular cardiotoxicity, over their parent compounds, while retaining their chemotherapeutic properties.

DESCRIPTION OF THE PRIOR ART

Adriamycin and daunorubicin are among the antineoplastic antibiotics from the antracycline group which are particularly valuable chemotherapeutics used in the treatment of cancer, primarily in the remission induction of myelocytic leukemia, as well as cancers of the breast, bladder, prostate and lymphomas. However, their practical therapeutic application in the treatment of neoplasm, that is, abnormal or cancerous tissue growth, is contraindicated by the occurrence of harmful side effects, particularly their considerable cardiotoxicity. These antibiotics have been known to induce cardiac failure or severe cardiac damage if certain total dosage levels are exceeded. Their toxicity is is also known to include bone marrow depression, alopecia and oro-gastrointestinal reactions. Hence, the accumulation of daunorubicin and adriamycin in tissue prohibits their use for more than 6 to 8 weeks and, thus, severely limits use in maintenance therapy.

Prior art efforts at reducing the cardiotoxicity of these antibiotics include their chemical modification. The most important of these modifications have lead to the production of the following derivatives: N,N-dibenzylodaunorubicin, G. Tong et al, *Journal of Medical Chemistry*, 1979, vol. 22, P. 911; 5-iminodaunorubicin, G. Tong et al, *Journal of Medical Chemistry*, 1979, vol. 22, P. 36; as well as Qualamycyne, the chelate of adriamycin with trivalent iron; M. Gosalvez et al, *European Journal of Cancer*, 1978, vol. 14, P. 1185.

OBJECT OF THE INVENTION

It is therefore an object of the present invention to provide enamine derivatives of the antineoplastic antibiotics daunorubicin and adriamycin useful in the treatment of neoplastic diseases, primarily leukemia.

It is a further objective of the present invention to provide enamine derivatives of daunorubicin and adriamycin which possess fewer harmful toxic side effects, in particular, cardiotoxicity.

SUMMARY OF THE INVENTION

The above objectives have been achieved and the disadvantages of the prior art overcome by the development of new enamine derivatives of daunorubicin and adriamycin of the general formula 1 and 2, wherein R denotes a hydrogen atom or a hydroxyl group.

The invention provides for a class of antibiotics useful in the treatment of cancer, particularly leukemia. More specifically, the inventive compounds are enamine derivatives of daunorubicin and adriamycin of the formula 1:

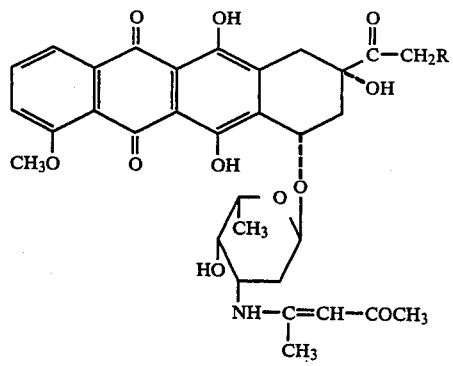

and formula 2:

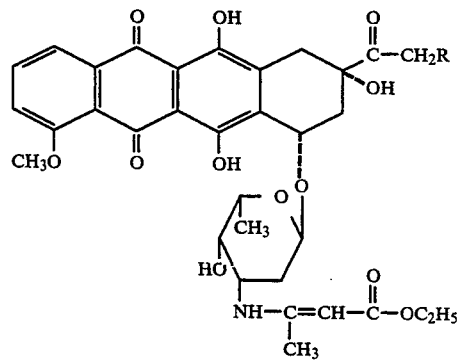

wherein R denotes a hydrogen atom or hydroxyl group.

As stated, the present derivatives retain their effectiveness as chemotherapeutic agents despite a structural change. However, electron absorption spectra and infra-red spectra indicate conservation in the inventive derivatives of an anthra-cycline ring, which accounts for the retention of antineoplastic activity. Additionally, mass spectrometry by field absorption, as well as elementary analysis of the obtained compounds give evidence of the presence of this structure.

Examination of the cardiac muscle of rats after the intraperitoneal administration of the parent compound, daunorubicin, and its enamine derivative according to the present invention, N-(1-carboethoxy-propen-1-yl-2)-daunorubicin, at 0.2, 10 and 20 mg/kg doses confirms that the present inventive compound causes considerably less morphological and ultrastructural changes to muscular tissue than does the initial daunorubicin.

Preparations from cardiac muscle tinted with H+E have been examined under light and polarizing microscopes. It has been demonstrated that daunorubicin administered in the three dosage levels above mentioned leads to the formation of numerous subsegmentary contractions causing, in effect, disturbances in heart rhythm. The present N-1-carboethoxy-propen-1-yl-2)-daunorubicin does not cause said disturbances, the cardiac muscle evidencing a regular and alternating system of isotropic and anizotropic fringes, D. Chibowski, Z. Siezienicwska, Z. Kleinrok, B. Chmielewska, "Morphological and Ultrastructural Exponents of Early Cardiotoxicity in Rats After the Administration of Rubidomycin and Its Derivatives"; Polish Pathology, 1983.

Hence, the present derivatives do not induce cardiac damage as do the prior art antineoplastic antibiotics, and their reduced toxicity indicates their ongoing use in cancer maintenance therapy.

Enamine derivatives of the antineoplastic antibiotics daunorubicin and adriamycin according to the present invention as well as a method for preparing the derivatives will be fully described by the following examples. These examples shall in no way be construed as limiting the scope of the subject matter of the present invention.

EXAMPLE I 0.53 gram of daunorubicin in a free base is dissolved in 100 ml of methylene chloride. 1 ml of ethyl acetylacetate is added to the solution by constant stirring. The entire mixture is agitated for 12 hours at room temperature in a nitrogenic atmosphere. The reaction is checked by means of thin-layer chromatography on a silica gel in a toluene-acetone system in a ratio of 8:1. The solution is then evaporated until a small volume of composition remains and, the final product is pecipitated by the addition of a mixture of ethyl ether and hexane in a ratio of 1:1. The precipitated results from the mixture of acetone and ethyl ether. 0.4 g of N-(1-carboethoxy-propen-1-yl-2)-daunorubicin is obtained which corresponds to 60 percent of the theoretical yield. The composition decomposes at 151°-154° C., M.S.F.D. m/z 639 (M+, 80 percent of relative intensity); 640 (M++1, 100 percent of relative intensity); IR (KBr)$\nu$=1590, 1610, 1650, 1670, 1715, 1720, cm$^{-1}$ (chelate and free carbonyl groups).

Elementary analysis of the formula $C_{33}H_{37}O_{12}N$ as calculated, in percent: C—61.96; H—5.83; N—2.19. Analysis of the compound actually obtained yields, in percent: C—61.74; H—5.98; N—2.01.

acetone is added to the solution, and it is agitated at room temperature for 12 hours in a nitrogenic atmosphere. The final product is separated as in example II and 0.04 g of N-(penten-2-on-4-yl-2) adriamycin is obtained corresponding to 60 percent of its theoretical yield. The composition decomposes at 210°-213° C., M.S.F.D. m/z 625 (M+, 100 percent of relative intensity).

Elementary analysis of the formula $C_{32}H_{35}O_{12}N$ as calculated theoretically, in percent: C—62.49; H—5.74; N—2.23. Analysis of the compound actually obtained, in percent: C—62.10; H—5.76; N—2.18.

EXPERIMENT I

The following Table I sets forth the comparative results of the effectiveness of the parent antibiotic, daunorubicin, in the inhibition of the growth of the cancerous cells of murine leukemia P-388 in mice versus the anticancer activity of enamine derivatives of daunorubicin according to the present invention. $ED_{50}$ denotes the concentration of the compound being tested leading to 50 percent inhibition of cancerous cell growth at 48 hours incubation time of the compound being tested. $LD_{50}$ indicates the dosage of the tested compounds which cause death after 24 hours of one-half of the number of mice which have been intraperitonically administered the subject compound. T/C in percent represents the ratio of mean survival time of the group of treated mice versus the group of untreated mice.

It is clearly demonstrated that the toxic effects of daunorubicin occur at a far lower dosage level as opposed to the inventive derivatives. At the same time, the antineoplastic activity of the present compounds compare favorably with the parent compound.

TABLE I

| Compounds tested | $ED_{50}$ (g/ml) | T/C (percent) Dose (mg/kg) | | | | | | | $LD_{50}$ (mg/kg) |
|---|---|---|---|---|---|---|---|---|---|
| | | 200 000 | 100 000 | 50 000 | 25 000 | 12 500 | 6 250 | 3 130 | |
| Daunorubicin | 0.01 | | | 102 | 127 | 112 | 112 | 108 | 135 |
| N—(1-carboethoxy propen-1-yl-2)-daunorubicin | 0.05 | 102 | 144 | 132 (128) | 115 (119) | 103 | 103 | 94 | 500 |
| N—(penten-2-on-4 yl-2)-daunorubicin | 0.05 | toxic | 147 | 118 (144) | 125 (131) | 119 | 110 | 131 | 500 |

EXAMPLE II 0.53 g of daunorubicin in the form of a free base is dissolved in 100 ml of methylene chloride. To this solution, 1 mg of acetylacetate is added, and the solution is agitated for 12 hours at room temperature in a nitrogenic atmosphere. The solution is thickened and precipitated with ethyl ether. 0.5 g of N-(penten-2-on-4-yl-2) daunorubicin is obtained which corresponds to 80 percent of the theoretical yield. The composition decomposes at 209°-210° C.; M.S.F.D m/z 609 (M+—80 percent of relative intensity); 610 (M++1, 100 percent of relative intensity) IR (KBr)$\nu$=1585, 1620, 1710 cm$^{-1}$ (chelate and free carbonyl groups). Elementary analysis of the formula $C_{32}H_{35}O_{11}N$ as calculated theoretically in percent: C—63.06; H—5.79; N—2.30. Analysis of the compound actually obtained yields, in percent: C—62.75; H—5.87; N—2.07.

EXAMPLE III 0.057 g of adriamycin in the form of a base is suspended in 20 ml of methylene chloride. 0.1 ml of acetyl-

We claim:
1. A compound consisting of the enamine derivative of daunorubicin and adriamycin of the formula 1:

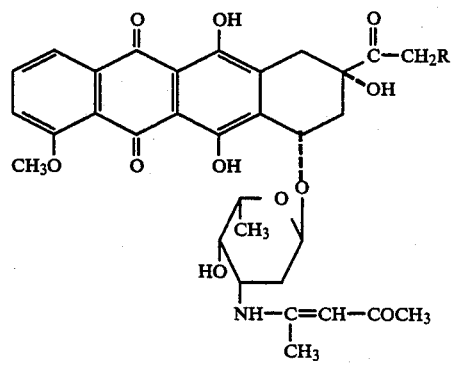

and formula 2:

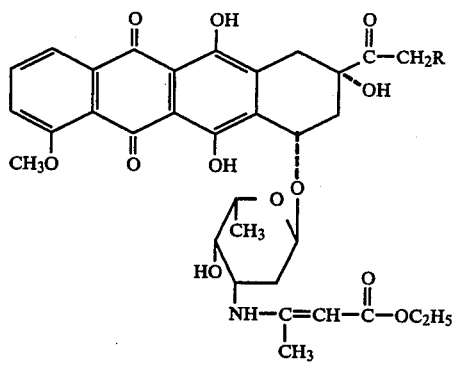
5
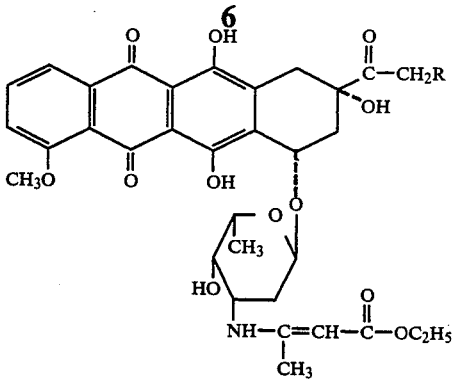
6
wherein R denotes a hydrogen atom or a hydroxyl group.
* * * * *
wherein R denotes a hydrogen atom or a hydroxyl group.
* * * * *